(12) United States Patent
Gresham

(10) Patent No.: US 8,241,251 B2
(45) Date of Patent: Aug. 14, 2012

(54) GEL SEAL FOR A SURGICAL TROCAR APPARATUS

(75) Inventor: Richard D. Gresham, Guilford, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 1791 days.

(21) Appl. No.: 10/925,850

(22) Filed: Aug. 25, 2004

(65) Prior Publication Data

US 2006/0047284 A1    Mar. 2, 2006

(51) Int. Cl.
*A61M 5/178* (2006.01)

(52) U.S. Cl. ......... 604/167.02; 604/167.01; 604/167.03; 604/167.04; 604/167.06; 604/164.01

(58) Field of Classification Search .................... 604/30, 604/164.01, 164.02, 167.01–167.04, 167.06, 604/256, 164.03–166.01; 606/108, 167, 606/185, 213
See application file for complete search history.

(56) References Cited

U.S. PATENT DOCUMENTS

| | | | |
|---|---|---|---|
| 3,402,710 A | 9/1968 | Paleschuck |
| 3,918,726 A | 11/1975 | Kramer |
| 4,447,237 A | 5/1984 | Frisch et al. |
| 4,475,548 A | 10/1984 | Muto |
| 4,519,908 A | 5/1985 | Woodruff |
| 4,610,665 A | 9/1986 | Matsumoto et al. |
| 5,015,228 A | 5/1991 | Columbus et al. |
| 5,041,095 A | 8/1991 | Littrell |
| 5,104,389 A | 4/1992 | Deem et al. |
| 5,127,626 A | 7/1992 | Hilal et al. |
| 5,180,376 A | 1/1993 | Fischell |
| 5,207,656 A | 5/1993 | Kranys |
| 5,330,497 A | 7/1994 | Freitas et al. |
| 5,338,313 A | 8/1994 | Mollenauer et al. |
| 5,342,315 A | 8/1994 | Rowe et al. |
| 5,360,417 A | 11/1994 | Gravener et al. |
| 5,389,080 A | 2/1995 | Yoon |
| 5,389,081 A | 2/1995 | Castro |
| 5,391,153 A | 2/1995 | Haber et al. |
| 5,407,434 A | 4/1995 | Gross |
| 5,429,609 A | 7/1995 | Yoon |
| 5,441,486 A | 8/1995 | Yoon |
| 5,460,616 A | 10/1995 | Weinstein et al. |
| 5,480,410 A | 1/1996 | Cuschieri et al. |
| 5,484,425 A | 1/1996 | Fischell et al. |
| 5,514,109 A | 5/1996 | Mollenauer et al. |

(Continued)

FOREIGN PATENT DOCUMENTS

AU    2005202133    12/2006

(Continued)

OTHER PUBLICATIONS

European Search Report.

(Continued)

*Primary Examiner* — Kevin C Sirmons
*Assistant Examiner* — Kami A Bosworth

(57) ABSTRACT

A seal assembly for use with an access device during a surgical procedure includes a housing having a passageway therethrough dimensioned to permit passage of a surgical instrument and being adapted for mounting to a trocar device, and a seal comprising a gel material and being mounted to the housing across the passageway. The seal includes inner seal portions defining an access channel dimensioned to form a substantial sealing relation with an object therethrough and substantially close in the absence of the surgical instrument. The seal preferably comprises a second material having a hardness greater than a hardness of the gel material. The gel material may be selected from the group consisting of urethane gel, silicone gel.

23 Claims, 6 Drawing Sheets

U.S. PATENT DOCUMENTS

| | | | |
|---|---|---|---|
| 5,514,133 | A | 5/1996 | Golub et al. |
| 5,542,931 | A | 8/1996 | Gravener et al. |
| 5,550,363 | A | 8/1996 | Obata et al. |
| 5,556,387 | A | 9/1996 | Mollenauer et al. |
| 5,603,702 | A | 2/1997 | Smith et al. |
| 5,628,732 | A | 5/1997 | Antoon, Jr. et al. |
| 5,634,908 | A | 6/1997 | Loomas |
| 5,634,937 | A | 6/1997 | Mollenauer et al. |
| 5,653,705 | A | 8/1997 | de la Torre et al. |
| 5,662,615 | A | 9/1997 | Blake, III |
| 5,722,958 | A | 3/1998 | Gravener et al. |
| 5,738,664 | A | 4/1998 | Erskine et al. |
| 5,741,298 | A | 4/1998 | MacLeod |
| 5,743,884 | A | 4/1998 | Hasson et al. |
| 5,779,697 | A | 7/1998 | Glowa et al. |
| 5,788,676 | A | 8/1998 | Yoon |
| 5,843,031 | A | 12/1998 | Hermann et al. |
| 5,906,577 | A | 5/1999 | Beane et al. |
| 5,957,913 | A | 9/1999 | de la Torre et al. |
| 5,989,233 | A | 11/1999 | Yoon |
| 6,017,356 | A | 1/2000 | Frederick et al. |
| 6,024,736 | A | 2/2000 | de la Torre et al. |
| 6,079,692 | A | 6/2000 | Powell |
| 6,110,154 | A | 8/2000 | Shimomura et al. |
| 6,315,770 | B1 | 11/2001 | de la Torre et al. |
| 6,319,246 | B1 | 11/2001 | de la Torre et al. |
| 6,355,014 | B1 | 3/2002 | Zadno-Azizi et al. |
| 6,440,063 | B1 | 8/2002 | Beane et al. |
| 6,482,181 | B1 | 11/2002 | Racenet et al. |
| 6,551,283 | B1 | 4/2003 | Guo et al. |
| 6,569,120 | B1 | 5/2003 | Green et al. |
| 6,602,240 | B2 | 8/2003 | Hermann et al. |
| 6,610,031 | B1 | 8/2003 | Chin |
| 6,663,598 | B1 | 12/2003 | Carrillo, Jr. et al. |
| 6,702,787 | B2 | 3/2004 | Racenet et al. |
| 6,712,791 | B2 | 3/2004 | Lui et al. |
| 7,052,454 | B2 | 5/2006 | Taylor |
| 7,153,261 | B2 | 12/2006 | Wenchell |
| 7,163,510 | B2 | 1/2007 | Kahle et al. |
| 7,235,062 | B2 | 6/2007 | Brustad |
| 7,244,244 | B2 | 7/2007 | Racenet et al. |
| 7,390,317 | B2 | 6/2008 | Taylor et al. |
| 7,473,221 | B2 | 1/2009 | Ewers et al. |
| 2001/0041871 | A1 | 11/2001 | Brimhall |
| 2001/0049499 | A1 | 12/2001 | Lui et al. |
| 2001/0049508 | A1 | 12/2001 | Fangrow, Jr. et al. |
| 2002/0013522 | A1 | 1/2002 | Lav et al. |
| 2002/0013552 | A1 | 1/2002 | Dennis |
| 2003/0032858 | A1 | 2/2003 | Ginn et al. |
| 2003/0040711 | A1 | 2/2003 | Racenet et al. |
| 2003/0050604 | A1 | 3/2003 | Lui et al. |
| 2003/0139756 | A1 | 7/2003 | Brustad |
| 2003/0195472 | A1 | 10/2003 | Green et al. |
| 2003/0208104 | A1 | 11/2003 | Carrillo, Jr. et al. |
| 2004/0015185 | A1 | 1/2004 | Ewers et al. |
| 2004/0054353 | A1 | 3/2004 | Taylor |
| 2004/0059297 | A1 | 3/2004 | Racenet et al. |
| 2004/0066008 | A1 | 4/2004 | Smith |
| 2004/0093018 | A1 | 5/2004 | Johnson et al. |
| 2004/0106942 | A1 | 6/2004 | Taylor et al. |
| 2004/0111060 | A1 | 6/2004 | Racenet et al. |
| 2004/0254426 | A1 | 12/2004 | Wenchell |
| 2005/0020884 | A1 | 1/2005 | Hart et al. |
| 2005/0059934 | A1 | 3/2005 | Wenchell et al. |
| 2005/0096605 | A1 | 5/2005 | Green et al. |
| 2005/0096695 | A1 | 5/2005 | Olich |
| 2005/0148823 | A1 | 7/2005 | Vaugh et al. |
| 2005/0165433 | A1 | 7/2005 | Haberland et al. |
| 2005/0212221 | A1 | 9/2005 | Smith et al. |
| 2005/0267419 | A1 | 12/2005 | Smith |
| 2006/0041232 | A1 | 2/2006 | Stearns et al. |
| 2006/0047284 | A1 | 3/2006 | Gresham |
| 2006/0047293 | A1 | 3/2006 | Haberland et al. |
| 2006/0084842 | A1 | 4/2006 | Hart et al. |
| 2006/0129165 | A1 | 6/2006 | Edoga et al. |
| 2006/0149305 | A1 | 7/2006 | Cuevas et al. |
| 2006/0224120 | A1 | 10/2006 | Smith et al. |
| 2006/0264991 | A1 | 11/2006 | Johnson et al. |
| 2006/0276751 | A1 | 12/2006 | Haberland et al. |
| 2007/0055107 | A1 | 3/2007 | Wenchell |
| 2007/0088241 | A1 | 4/2007 | Brustad et al. |
| 2007/0116854 | A1 | 5/2007 | Taylor et al. |
| 2007/0151566 | A1 | 7/2007 | Kahle et al. |
| 2007/0197972 | A1 | 8/2007 | Racenet et al. |
| 2007/0233006 | A1 | 10/2007 | Brustad |
| 2008/0011307 | A1 | 1/2008 | Beckman et al. |
| 2008/0033363 | A1 | 2/2008 | Haberland et al. |
| 2008/0077169 | A1 | 3/2008 | Taylor et al. |
| 2008/0086074 | A1 | 4/2008 | Taylor et al. |
| 2009/0048683 | A1 | 2/2009 | Morris et al. |

FOREIGN PATENT DOCUMENTS

| | | |
|---|---|---|
| DE | 3217118 | 8/1983 |
| DE | 3737121 | 5/1989 |
| EP | 0051718 | 5/1982 |
| EP | 0113520 | 7/1984 |
| EP | 0169787 | 1/1986 |
| EP | 0312219 | 4/1989 |
| EP | 0538060 | 4/1993 |
| EP | 1629787 | 1/2006 |
| EP | 1698291 | 6/2006 |
| GB | 1482857 | 8/1977 |
| JP | 58163867 | 9/1983 |
| JP | 5-103854 | 4/1993 |
| JP | 06061518 | 4/1994 |
| JP | 07241298 | 9/1995 |
| WO | 93/04717 | 3/1993 |
| WO | 94/17844 | 8/1994 |
| WO | 95/13313 | 5/1995 |
| WO | 98/53865 | 3/1998 |
| WO | 02/087682 | 11/2002 |
| WO | WO 02/087682 | 11/2002 |
| WO | 03/011154 | 2/2003 |
| WO | WO 03/011154 A | 2/2003 |
| WO | 2004/043275 | 5/2004 |
| WO | WO 2004/043275 | 5/2004 |
| WO | 2007/119232 | 10/2007 |

OTHER PUBLICATIONS

Hong T. et al., Development of in Vitro Performance Tests and Evaluation of Nonabsorbable Monofilament Sutures for Cardiovascular Surgery, ASAIO Journal, vol. 44, No. 6, Nov. 1998.

Hong T. et al., Development of in Vitro Performance Tests and Evaluation of Nonabsorbable Monofilament Sutures for Cardiovascular Surgery, ASIAO Journal, vol. 44, No. 6, Nov. 1998.

European Search Report, corresponding to European application No. 05-17503.3-2318, dated Dec. 18, 2005 (6 pages).

European Search Report for corresponding European Application No. 05017503.3-2318 dated Mar. 23, 2006 (3 pages).

European Search Report, Application No. EP 08253234, dated Jan. 30, 2009.

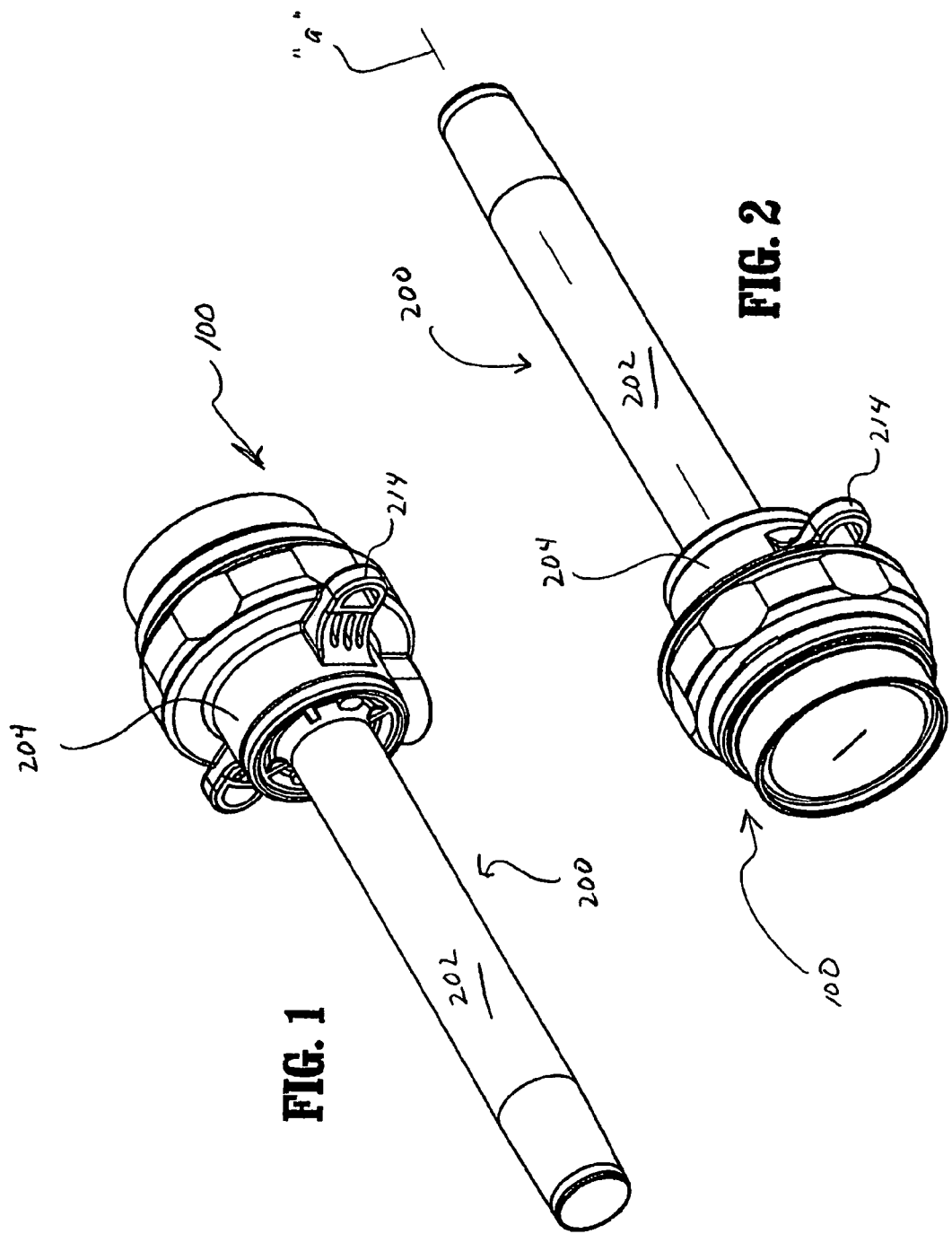

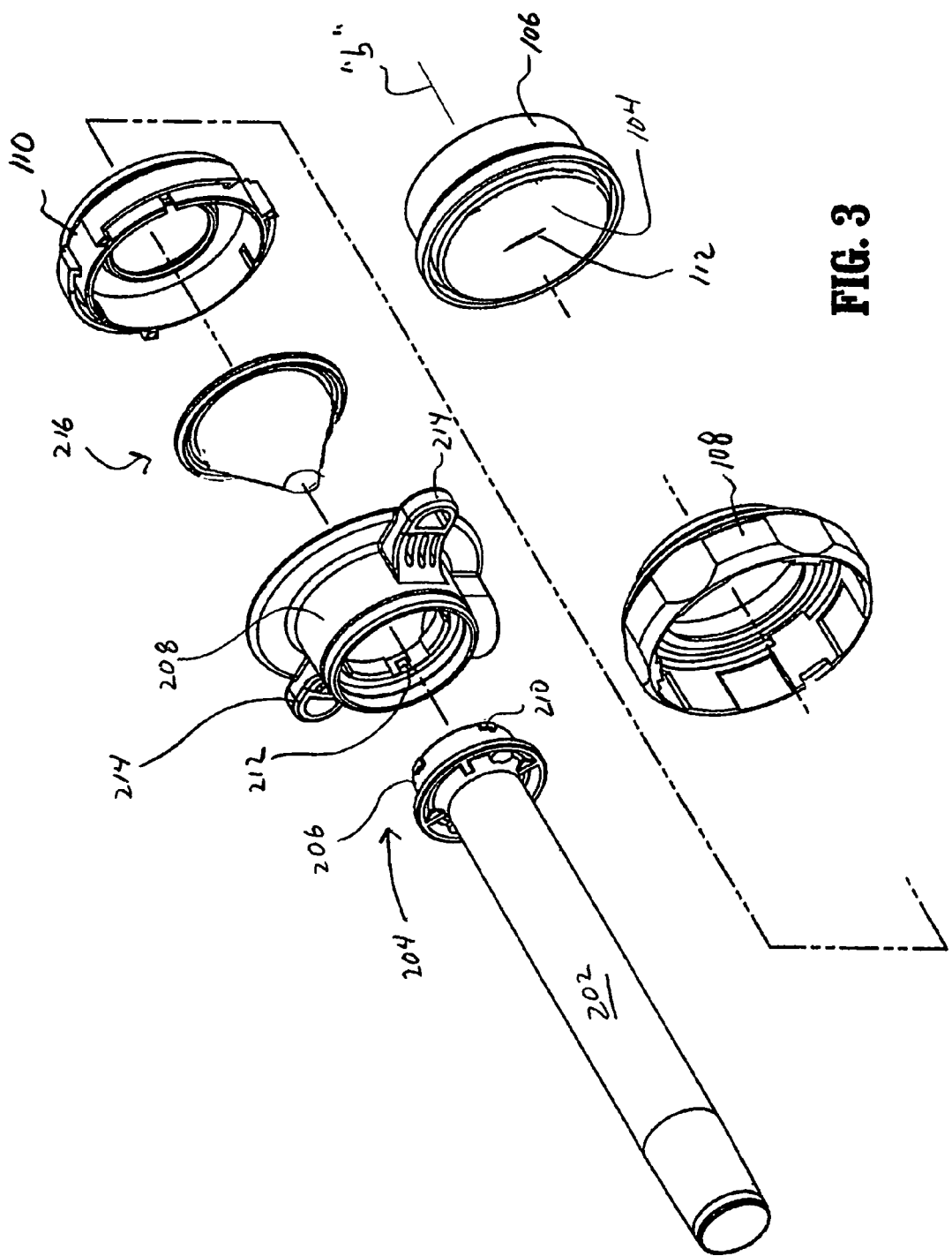

GEL SEAL FOR A SURGICAL TROCAR APPARATUS

BACKGROUND

1. Field of the Disclosure

The present disclosure relates to surgical devices and more particularly to a seal assembly for use with a surgical access device during a minimally invasive surgical procedure.

2. Description of the Related Art

Minimally invasive surgical procedures including both endoscopic and laparoscopic procedures permit surgery to be performed on organs, tissues and vessels far removed from an opening within the tissue. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. These procedures typically employ surgical instruments which are introduced into the body through a cannula. The cannula has a seal assembly associated therewith. The seal assembly provides a substantially fluid tight seal about the instrument to preserve the integrity of the established pneumoperitoneum.

Minimally invasive procedures have several advantages over traditional open surgery, including less patient trauma, reduced recovery time, reduced potential for infection, etc. . . . However, despite its recent success and overall acceptance as a preferred surgical technique, minimally invasive surgery, such as laparoscopy, has several disadvantages. In particular, the maintenance of the seal about the surgical instrument has proved to be difficult in certain procedures, e.g., in procedures requiring extensive manipulation of the long narrow endoscopic instruments within a remote site. In addition, known seal devices are deficient in closing the opening defined by the seal in the absence of an instrument.

SUMMARY

Accordingly, the present disclosure is directed to a seal assembly for use with an access device during a surgical procedure. The seal assembly includes a housing having a passageway therethrough dimensioned to permit passage of a surgical instrument and being adapted for mounting to a trocar device, and a seal comprising a gel material and being mounted to the housing across the passageway. The seal includes inner seal portions defining an access channel dimensioned to form a substantial sealing relation with an object therethrough and substantially close in the absence of the surgical instrument. The seal preferably comprises a second material having a hardness greater than a hardness of the gel material. The gel material may be selected from the group consisting of a urethane gel, a silicone gel, gels incorporating super absorbent polymers, alginates, gum Arabic, polymer hydrogels or a copolymer thereof, or any combination of these materials. A lubricious coating may be applied to the gel material.

In another embodiment, a surgical access device includes an access member defining a central longitudinal axis and having a central opening dimensioned for passage of an object, and a seal member mounted to the access member and being adapted to permit passage of the object. The seal member includes first and second seal materials. The first material may comprise a relatively soft gel while the second seal material is more rigid than the soft gel of the first material to stabilize the seal member and provide a substantial sealed relation with the object. The second seal material may comprise an elastomer material and/or a fabric material.

In another embodiment, a surgical access device includes an access member defining a central longitudinal axis and having a central opening dimensioned for passage of an object, and a seal member mounted to the access member. The seal member defines an access channel to permit passage of the object. The seal member includes a first seal element and a second seal element. The first seal element comprises a relatively soft gel material while the second seal element comprises a material being more rigid than the soft gel material to stabilize the seal member and provide a substantial sealed relation with the object. The soft gel material of the first seal element may comprise one of a urethane gel or a silicone gel. The material of the second seal element is selected from the group consisting of elastomers and fabrics.

In one embodiment, the first seal element includes inner portions defining an access channel for permitting passage of an object in substantial sealed relation therewith. The second seal element includes inner portions adapted to permit passage of the object. The inner portions of the second seal element may define an opening adapted to form a sealed relation with an object inserted therethrough. The first seal element may be mounted to the second seal element. In the alternative, the first seal element is proximal of the second seal element. In yet another alternative, the second seal element is embedded within the first seal element. The second seal element may define a general dome-shaped configuration. The second seal element may include one of a duck-bill seal, conical seal and septum seal. The first seal element may be adapted for lateral movement relative to the longitudinal axis of the access member.

BRIEF DESCRIPTION OF THE DRAWING(S)

Preferred embodiments of the present disclosure will be better appreciated by reference to the drawings wherein:

FIGS. 1-2 are perspective views of a cannula assembly and a seal assembly in accordance with the principles of the present disclosure;

FIG. 3 is a perspective view with parts separated of the cannula and seal assemblies of FIG. 1;

DETAILED DESCRIPTION OF THE PREFERRED EMBODIMENT(S)

Figure 4:
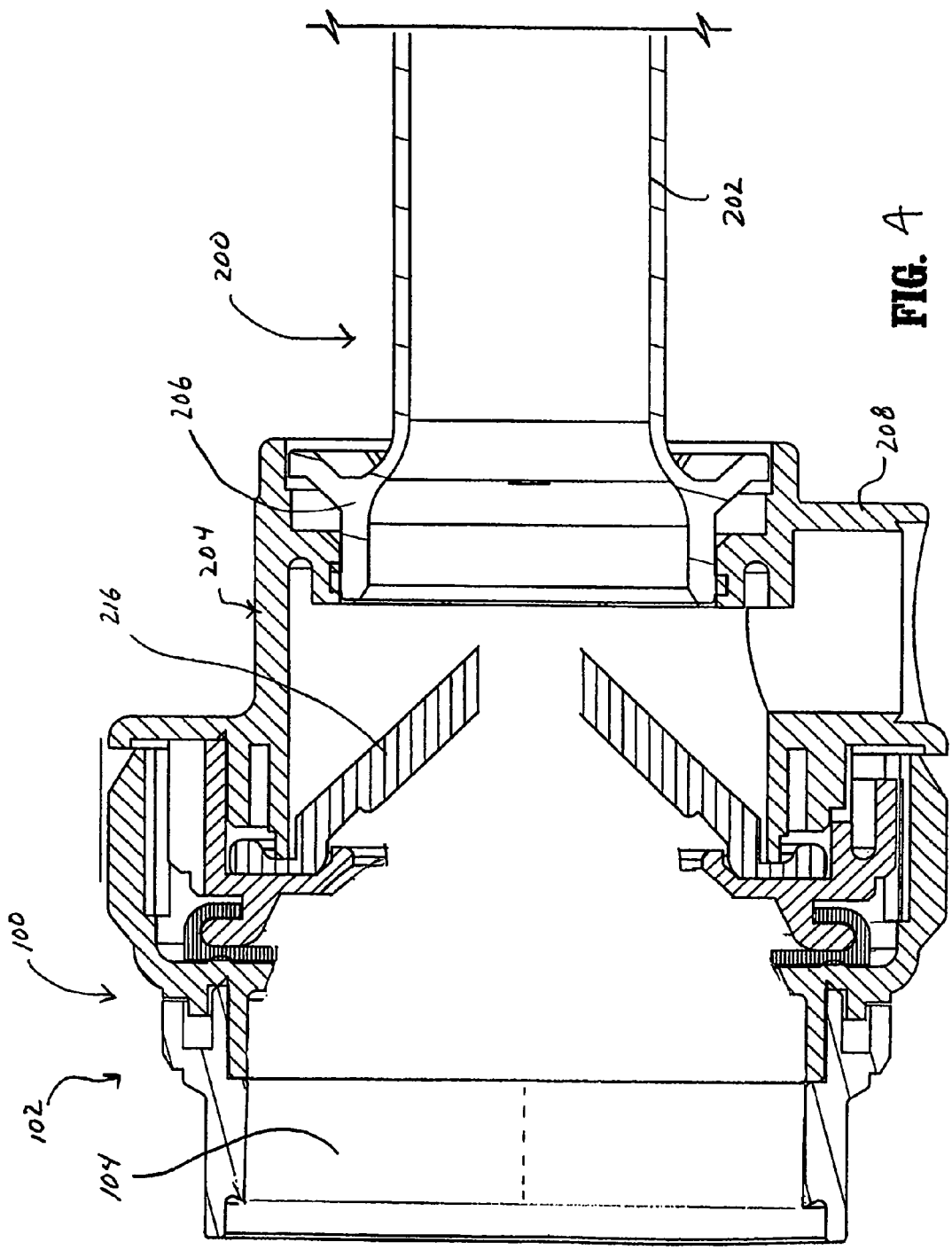
FIG. 4 is a side cross-sectional view of the cannula and seal assemblies.

The seal assembly of the present disclosure, either alone or in combination with a seal system internal to a cannula assembly, provides a substantial seal between a body cavity of a patient and the outside atmosphere before, during and after insertion of an object through the cannula assembly. Moreover, the seal assembly of the present invention is capable of accommodating objects of varying diameters, e.g., instruments from about 4.5 mm to about 15 mm, by providing a gas tight seal with each instrument when inserted. The flexibility of the present seal assembly greatly facilitates endoscopic surgery where a variety of instruments having differing diameters are often needed during a single surgical procedure. The seal assembly is further adapted to substantially close in the absence of a surgical instrument to maintain the integrity of the insufflated peritoneal cavity.

The seal assembly contemplates the introduction and manipulation of various types of instrumentation adapted for insertion through a trocar and/or cannula assembly while maintaining a fluid tight interface about the instrumentation to preserve the atmospheric integrity of a surgical procedure from gas and/or fluid leakage. Specifically, the seal assembly accommodates angular manipulation of the surgical instrument relative to the seal axis. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation".

Moreover, the seal assembly may be readily incorporated into an access device, such as a conventional trocar device or cannula housing to provide the device with zero-closure and/or sealing around an instrument or other object.

The seal assembly may also be adapted to receive and form a seal about a physician's arm or hand during a hand-assisted laparoscopic procedure. In this application, the seal assembly is a component of an access member which is introduced within the body to provide access to underlying tissue in, e.g., the abdominal cavity.

Referring now to the drawings, in which like reference numerals identify identical or substantially similar parts throughout the several views, FIGS. 1-2 illustrate the seal assembly 100 of the present disclosure mounted to an access device such as cannula or trocar assembly 200. Cannula assembly 200 may be any conventional cannula suitable for the intended purpose of accessing a body cavity and typically defines a passageway permitting introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown) which may be blunt, a non-bladed, or a sharp pointed instrument positionable within the passageway of the cannula assembly 200. The obturator assembly is utilized to penetrate the abdominal wall or introduce the cannula assembly 200 through the abdominal wall, and then subsequently is removed from the cannula assembly to permit introduction of the surgical instrumentation utilized to perform the procedure through the passageway.

Cannula assembly 200 includes cannula sleeve 202 and cannula housing 204 mounted to an end of the sleeve 202. Cannula sleeve 202 defines a longitudinal axis "a" extending along the length of sleeve 202. Sleeve 202 further defines an internal longitudinal passage dimensioned to permit passage of surgical instrumentation. Sleeve 202 may be formed of stainless steel or other rigid materials such as a polymeric material or the like. Sleeve 202 may be clear or opaque. The diameter of sleeve 202 may vary, but typically ranges from about 4.5 to about 15 mm for use with the seal assembly 100 of the present disclosure.

Cannula housing 204 includes two components, specifically, housing flange 206 which is attached to the proximal end of cannula sleeve 202 and main housing 208 as shown in FIGS. 3-4. Main housing 208 is connectable to housing flange 206 through a bayonet coupling consisting of radially spaced tongues 210 on the exterior of housing flange 206 and corresponding recesses 212 within the interior of main housing 208. Tongues 210 are receivable within recesses 212. Thereafter, housing flange 206 and main housing 208 are rotated to securely lock the tongues 210 within the recesses 212. Other conventional means, e.g., a threaded snap fit, ultrasonic welding or any other means envisioned by one skilled in the art including, e.g., adhesive means, may be incorporated to connect housing flange 206 and main housing 208. Main housing 208 further includes diametrically opposed housing grips 214 dimensioned and arranged for gripping engagement by the fingers of the user. Additionally or alternatively, suture anchors may extend from main housing 208. Although shown and described as two components, cannula housing 204 may be a single component and attached to cannula sleeve 202 by any of the aforementioned means. The housing flange 206, or the housing flange 206 and main housing 208, may be integrally formed with cannula sleeve 202.

With reference to FIG. 3, in conjunction with FIGS. 1-2, cannula housing 204 further includes valve 216. Valve 216 may be frusto-conical in shape and define an aperture for sealed reception of the instrument. In the alternative, valve 216 may be a flat disc-shaped valve, balloon valve, flapper valve, duck-bill valve etc. . . . The valve 216 may comprise a flat disc-shaped, conical, or hourglass-shaped member including a fabric material molded with an elastomer. The seals disclosed in certain embodiments of U.S. patent application Ser. No. 10/165,133, filed Jun. 6, 2002, the disclosure of which is hereby incorporated by reference, may be used. In a further alternative, valve 216 is preferably a fabric seal and is desirably arranged so as to have a constriction. For example, the valve may have the general shape of an hourglass. The fabric can be a woven material, a braided material, or a knitted material. The type of material is selected to provide a desired expansiveness. For example, a braid of varying end count and angle may be selected. A preferred material is a synthetic material such as nylon, Kevlar (Trademark of E.I. DuPont de Nemours and Company) or any other material that will expand and compress about an instrument inserted therethrough. The selected material desirably minimizes or prevents the formation of gaps when the instrument is introduced into the seal or valve 216. The material of valve 216 may be porous or impermeable to the insufflation gas. If porous, valve 216 may include a coating of a material which is impermeable to the insufflation gas or at least a portion of the valve may be coated. In addition, the fabric may be coated on its interior with urethane, silicone or other flexible lubricious materials to facilitate passage of an instrument or other object, such as the hand and arm, through the valve 216. In certain embodiments, the fabric is twisted about the axis "a" so as to form a constriction or closed portion. The fabric is desirably constructed of a material and/or arranged so that the fabric forms a constriction or closure. The seal may also be molded so as to have a constriction or may be knitted, braided or woven so as to have a constriction. Other arrangements for valve 216 are also envisioned. In further embodiments, valve 216 is omitted.

Referring now to FIGS. 3-4, in conjunction with FIGS. 1-2, seal assembly 100 will be discussed in detail. Seal assembly 100 includes seal housing, generally identified as reference numeral 102, and gel seal 104 which is disposed within the seal housing 102. Seal housing 102 houses the sealing components of the assembly and defines the outer valve or seal body of the seal assembly 100. Seal housing 102 defines central seal housing axis "b" which is preferably parallel to the axis "a" of cannula sleeve 202 and, more specifically, coincident with the axis "a" of the cannula. Seal housing 102 incorporates three housing components, namely, proximal, distal and inner housing components 106, 108, 110, respectively, which, when assembled together, form the seal housing 102. Assembly of housing components 106, 108, 110 may be effected by any of the aforementioned connection means discussed with respect to cannula housing 204. Although shown and described as three components, it is appreciated that seal housing 102 may be a single component having the gel seal mounted therein.

With particular reference to FIGS. 3-4, gel seal 104 will be discussed in detail. In the preferred embodiment, gel seal 104 is mounted to proximal housing component 106 through, e.g., conventional means, such as by adhering the gel seal 104 to the component 106 or molding the gel seal 104 in the component 106. Gel seal 104 is fabricated from an elastomer such as a soft urethane gel, silicone gel, etc. and preferably has compressible characteristics to permit the seal to receive objects having a variety of sizes, to conform and form a seal about the outer surface of the inserted object, and to close upon removal of the object. Gel seal 104 preferably includes a single slit 112 advantageously dimensioned to permit reception and passage of a surgical instrument. In particular, slit 112 opens to permit passage of the surgical instrument whereby the internal gel portions defining the slit 112 engage the instrument in sealed relation therewith. The slit 112 is further adapted to assume a substantially closed position upon removal of the instrument. In this position, the seal 104 prevents the egress of gaseous matter through seal housing 102. Slit 112 may have shapes other than that of a linear slit, such as "t"-shaped, "x" shaped, helical, etc.

Figure 5:
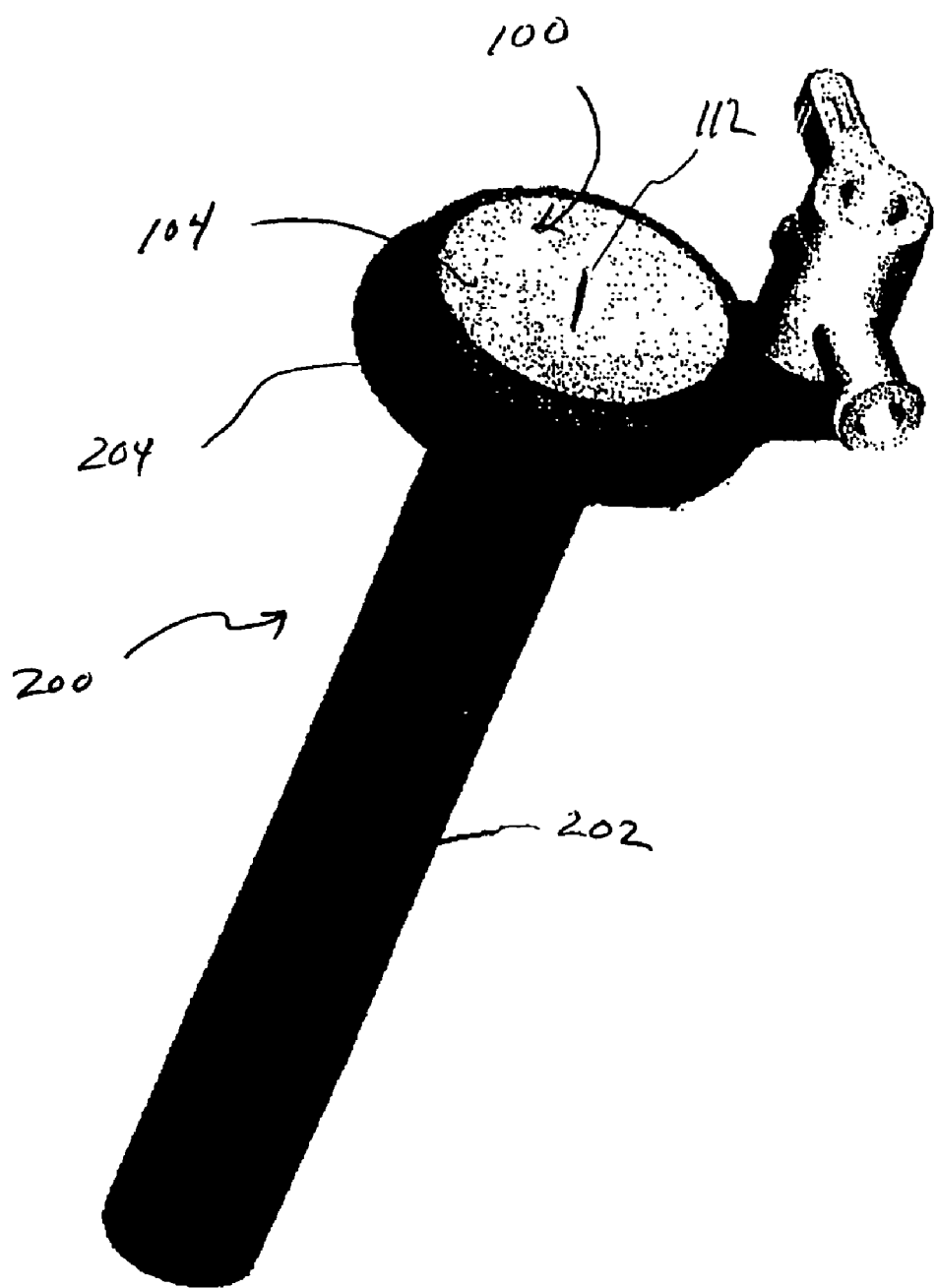
FIG. 5 is a perspective view illustrating the seal assembly incorporated within the cannula housing.

Seal assembly 100 may be associated with, or joined to, cannula assembly 200 in a variety of ways. In a preferred embodiment, seal housing 102 of seal assembly 100 and cannula housing 204 of cannula assembly 200 are adapted to detachably engage each other, e.g., through a bayonet lock, threaded attachment, latching attachment, or like mechanical means. In further embodiments, cannula housing 204 and valve 216 may be omitted and seal assembly 100 may be removably or permanently attached to flange 206. The seal assembly may be mounted to cannula assembly 100 before during or after application of the cannula assembly within the operative site. Alternatively, the seal assembly 100 may be built within cannula housing 204 as depicted in FIG. 5. As a further alternative, seal assembly 100 may be incorporated within a housing of a hand access device utilized in hand-assisted laparoscopic procedures.

The use of the seal assembly 100 and cannula assembly 200 in connection with introduction of a surgical instrument will be discussed. Seal assembly 100 is mounted to cannula assembly 200 and cannula assembly 200 is introduced into an insufflated abdominal cavity. An object, e.g., an instrument, is inserted into seal assembly 100 through slit 112 whereby the portions defining the slit 112 stretch to accommodate the instrument diameter, as necessary. The instrument is distally passed through the valve 216 in sealed relation therewith and into the body cavity to perform the desired procedure. The instrument is removed and the slit 112 of the gel seal 104 substantially closes to a zero-closure position to maintain the integrity of the established pneumoperitoneum. Other instruments may be introduced through the seal assembly 100 and cannula assembly to perform further operative techniques as desired.

FIGS. 6-13 illustrate various alternate embodiments of the gel seal 104 of FIGS. 1-4. Each embodiment includes a seal assembly fabricated from a first generally soil gel material and a second generally harder seal material which is mounted to or embedded within the soil gel material. The combination of materials of varying hardness aids in sealing instruments during manipulation. In one embodiment, the soft gel material may be any suitable material identified hereinabove in connection with the embodiment of FIGS. 1-4, including, for example a urethane gel, a silicone gel, gels incorporating super absorbent polymer, alginates, gum Arabic, polymer hydrogels or a copolymer thereof, or other flexible lubricous material, or any combination of these materials. In one preferred embodiment, the soil gel material comprises urethane. The second material mounted to, or embedded in, the soft gel material may include a relatively hard gel material, e.g., a urethane treated to be more rigid than the soft urethane or any of the aforementioned seal materials specifically treated to increase its respective rigidity. The second material may comprise any elastomeric material. Additionally or alternatively, the second material is a fabric material including a woven, braided or knitted material of the type discussed hereinabove in connection with the embodiment of FIGS. 1-4. In one preferred embodiment, the second material is the fabric seal disclosed in commonly assigned U.S. patent application Ser. No. 10/165,133, filed Jun. 6, 2002, the contents of which are incorporated by reference. The seal disclosed in the '133 application may be a flat septum seal having a first layer of resilient material and a second fabric layer juxtaposed relative to the first layer. The fabric layer may include a SPANDEX material.

Figure 6:
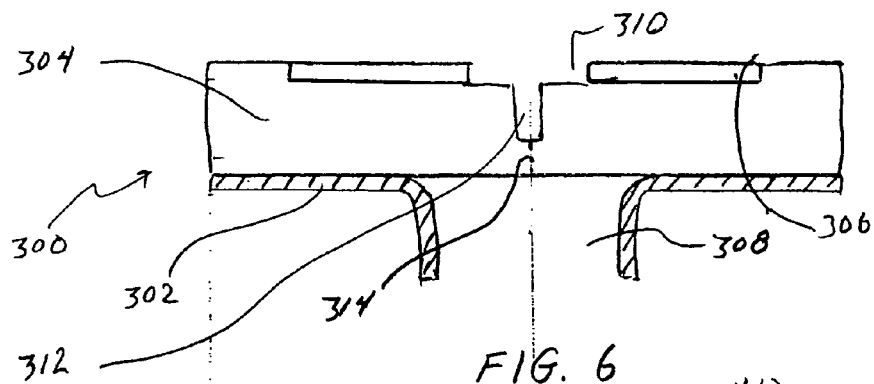
FIGS. 6-13 are side cross-sectional views of alternate embodiments of the seal assembly of FIG. 1.

With reference now to FIG. 6, one alternate embodiment of the seal assembly 300 includes base plate 302, soft urethane seal 304 mounted to the base plate 302 and fabric seal 306. Soft urethane seal 304 is mounted to base plate 302 through conventional means including adhesives, cements, etc. Alternatively soft seal 304 may be cast molded with base plate 302 during manufacture and secured to the base plate 302 during curing of the soft seal 304. Base plate 302 may be formed from an elastomer, preferably, urethane, having a greater rigidity than the urethane material of soft seal 304. Other elastomer materials are also envisioned. Base plate 302 defines an opening 308 dimensioned to permit passage of an object.

Fabric seal 306 is preferably embedded within the proximal end of soft urethane seal 304 of the gel seal assembly 300. For example, fabric seal 306 may be positioned within soft urethane seal 304 during manufacture of the seal whereby the fabric seal 306 is embedded upon a curing phase of the seal. Alternatively, fabric seal 306 may be secured to a proximal end of gel seal 304 with adhesives, cements etc. Fabric seal 306 defines an aperture 310 which permits reception of the object in sealed relation therewith.

Fabric seal 306 provides a degree of rigidity to gel seal 304 and may desirably assist in maintaining the gel seal 304 in its disc-shaped configuration. Moreover, the combination of fabric seal 306 and gel seal 304 defines a seal having enhanced adaptability to a variety of different diameter objects, e.g., instruments, and which maintains a seal upon offset manipulation of the object. Fabric seal 306 also serves as a secondary seal supplemental to the sealing functions of gel seal 304.

In a preferred embodiment, gel seal 304 includes a cored hole 312 disposed in the proximal end of gel seal 304. Cored hole 312 may extend completely through gel seal 304 or partially through the seal 302. In the partial arrangement of cored hole 312, cored hole 312 terminates in slit 314 which extends to the lower end of the seal 302. Cored hole 312 is advantageously dimensioned to facilitate reception and passage of an object, e.g., a surgical instrument through seal 300. Cored hole 312 and slit 314 may open to permit passage of the object whereby the internal gel portions defining the cored hole 312 and slit 314 engage the instrument in sealed relation therewith.

It is further envisioned that base plate 302, which incorporates a more rigid, e.g., elastomer material relative to the soft gel 304, may also serve as a seal in the event a larger sized object is positioned within seal assembly 300. In particular, the inner portions of base plate 302 defining opening 308 may readily adapt to form a seal about the inserted object.

Figure 7:
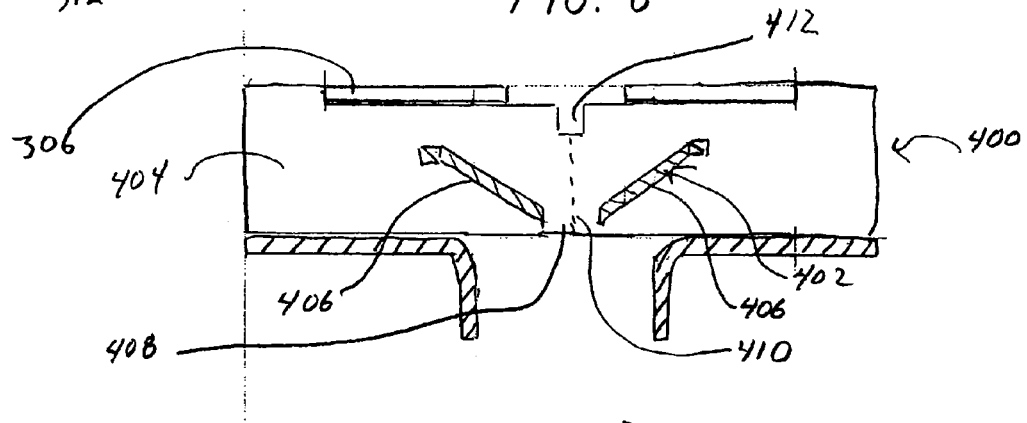

Referring now to FIG. 7, another alternate embodiment of the gel seal assembly is disclosed. Gel seal assembly 400 is similar to the embodiment of FIG. 6 and further includes a duck-bill seal 402 embedded within the main body section of gel seal 404. Duck bill seal 402 may be cast within gel seal 404 during manufacture and curing of the gel seal 404. Duck bill seal 402 preferably includes an elastomeric material and has a pair of planar seal portions 406 which taper inwardly relative to the axis of the seal. In one embodiment, duck bill seal 402 is a zero-closure valve, i.e., it substantially closes in the absence of an instrument. In the alternative, planar seal portions 406 do not close completely as depicted in FIG. 7. With this embodiment, a small gel section 408 of soft urethane material is disposed adjacent the distal or outlet opening of duck bill seal 402 to provide zero closure capabilities. This small gel section 408 preferably incorporates a slit 410 to permit passage of the object. Alternately, a gel section 408 may be secured within the interior of duck bill seal 402 adjacent its distal end. A cored hole 412 preferably extends from the aperture of the fabric seal to gel section 408 and is in communication with slit 410 of the gel section 408. The duckbill seal 402 may be substituted with a conical seal.

Figure 8:
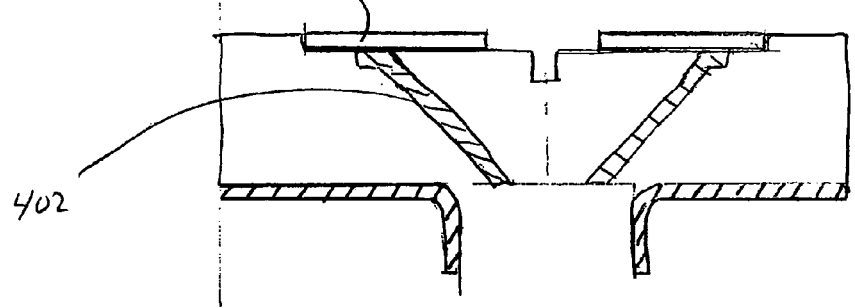

FIG. 8 illustrates a further embodiment of the embodiment of FIG. 7 where the duck bill seal 402 adjacent the proximal end of the seal 400 is in direct contact with the flat fabric seal 306 as shown. In addition, the size of the opening between the panel portions may be larger as shown in FIG. 8. It is also envisioned that the duck bill seal 402 may be substituted with a conical or frusto-conical seal of the type which defines an opening in its initial state and which expands upon passage of the object.

Figure 9:
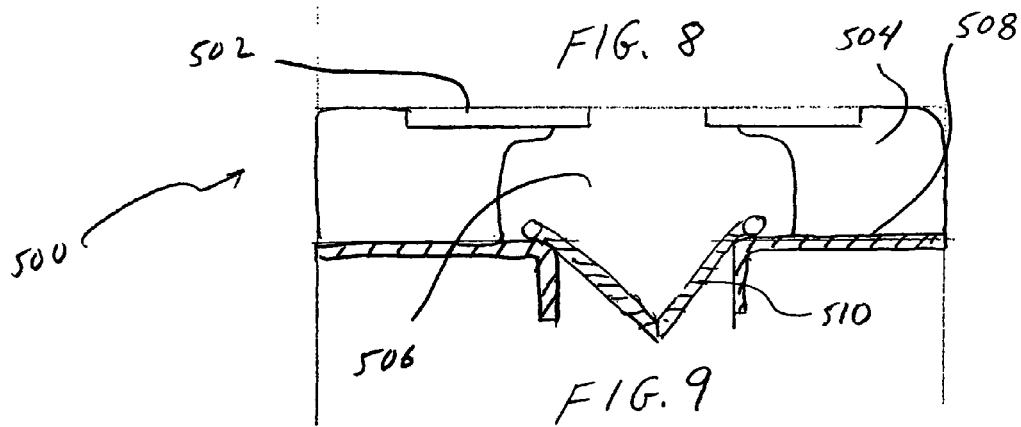

FIG. 9 illustrates an alternate embodiment of the seal assembly of the present disclosure. Gel seal assembly 500 includes flat fabric seal 502 embedded within soft urethane seal 504 in a manner similar to the embodiment of FIG. 5. Soft seal 504 further includes central open area 506 which is devoid of gel material. Central open area 506 facilitates passage of larger diameter objects, e.g., a surgeon's hand or instrumentation through seal assembly 500. Mounted within central open area 506 and extending within base plate 508 is a duck bill seal 510. Duck bill seal 510 functions as a zero-closure valve as discussed hereinabove.

Figure 10:
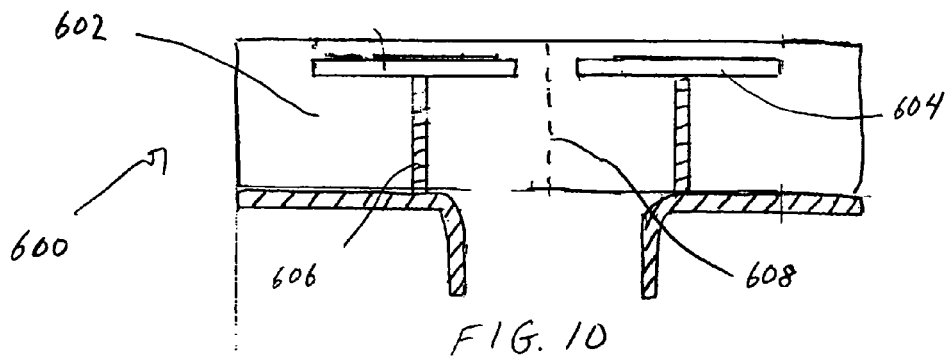

FIG. 10 illustrates an alternate embodiment including a gel seal assembly 600 having soft gel seal 602, flat seal 604 embedded within the gel seal 602 and cylindrical insert 606 which is embedded within the soft gel seal 602. Gel seal 602 defines an internal slit 608 adjacent its proximal end for passage of the object. Flat seal 604 may be an elastomeric seal or a fabric seal. Cylindrical insert 606 may be made from an elastomer or from a gel material having a greater hardness than the material of soft gel seal 602. Flat seal 604 and insert 606 serve as a stabilizer for the seal assembly 600 by increasing the overall rigidity of the seal 600. Flat seal 604 also functions as a secondary seal supplementing the sealing functions of gel seal 602.

Figure 11:
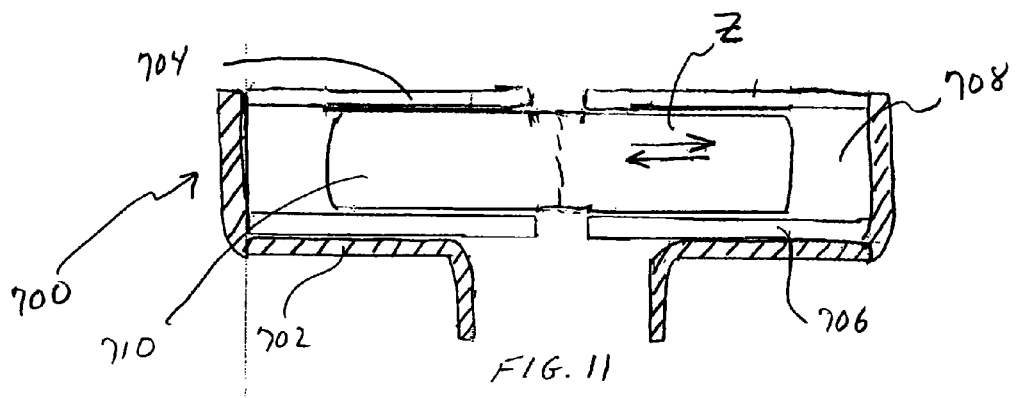

FIG. 11 illustrates yet another embodiment of the present disclosure. Seal assembly 700 includes housing 702 and first and second flat seals 704, 706 mounted adjacent a soft gel seal 710. Soft gel seal 710 is disposed within channel 708 and is adapted for radial movement within the channel 708. More specifically, gel seal 710 may move within channel 708 in the direction of directional arrows "Z" upon offset manipulation of the object, i.e., the soft gel seal 710 may free float within housing 702. A lubricious coating may be applied to gel seal 710 to facilitate this radial or traversing movement within channel 708. First and second seals 704, 706 may be elastomeric or incorporate a fabric material. Seals 704, 706 may include an aperture or incorporate a slit(s) to permit passage of the object. Alternatively, soft gel seal 710 may be mounted to either or both first and second flat seals 704, 706 and may or may not be adapted for radial movement within housing 702. One or both of seals 704, 706 may be omitted. In the embodiments of FIGS. 6-13, the gel seal may be mounted for movement (axial or radial) within housing 702.

Figure 12:
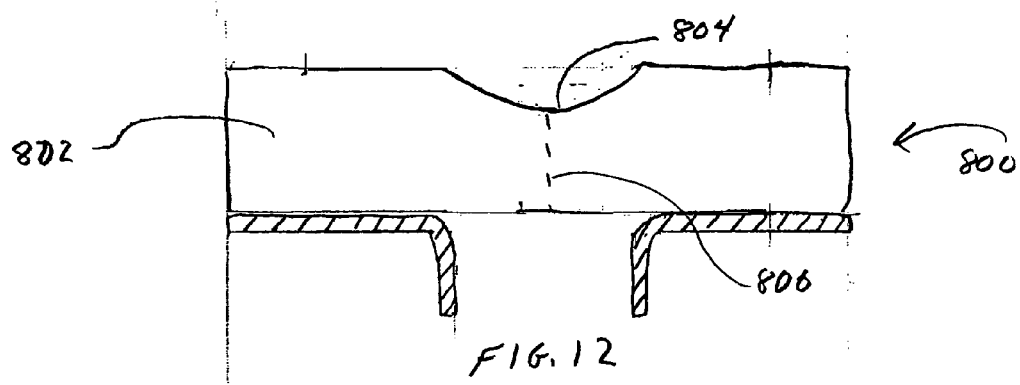

FIG. 12 illustrates another alternate embodiment of the present disclosure. Gel seal assembly 800 includes soft seal 802 with a bowled recess 804 within the proximal end of the soft gel seal 802. The bowled recess 804 extends to a narrow slit 806 which terminates within the distal side of soft seal 802. Slit 806 permits the instrument to pass through the seal 802 in sealing relation therewith. Slit 806 closes in the absence of an instrument. Bowled recess 804 effectively removes gel material adjacent slit 806 to facilitate passage of the object.

Figure 13:
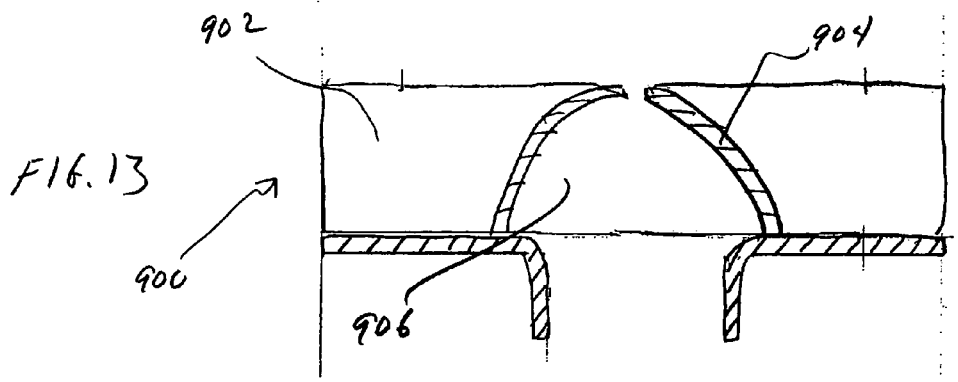

FIG. 13 illustrates yet another further embodiment of the seal of the present disclosure. Gel seal assembly 900 includes soft gel seal 902 and domed fabric seal 904 which is embedded within the gel seal 902. The central area 906 within domed fabric seal 904 may be filled with soft gel material or alternately free of material to facilitate passage of the object therethrough. In the embodiment of FIGS. 6-13, the gel seal may be mounted for movement within a housing.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A seal assembly for use with a trocar device, which comprises:
    a housing defining a longitudinal axis and having a passageway therethrough dimensioned to permit passage of a surgical instrument, the housing adapted for mounting to a trocar device;
    a first seal comprising a gel material and being mounted to the housing across the passageway, the first seal including inner seal portions defining an access channel dimensioned to form a substantial sealing relation with and in direct contact with the surgical instrument when advanced along the passageway;
    a second seal comprising a material having a hardness greater than a hardness of the gel material, the second seal embedded within and in direct contact with the first seal in the absence of the surgical instrument, the second seal arranged to stabilize the first seal and to receive the surgical instrument in substantial sealed relation, the second seal including one of a conical seal and a duckbill seal; and
    a third seal comprising a material having a hardness greater than a hardness of the gel material, the third seal disposed at a proximal end of the first seal, the third seal arranged to maintain the configuration of the first seal.

2. The seal assembly according to claim 1 wherein the gel material comprises a flexible lubricious material.

3. The seal assembly according to claim 1 wherein the gel material is selected from the group consisting of a urethane gel, a silicone gel, gels incorporating super absorbent polymers, alginates, gum Arabic, polymer hydrogels or a copolymer thereof, or any combination of these materials.

4. The seal assembly according to claim 1 further comprising a lubricious coating.

5. The seal assembly according to claim 1 wherein an upper surface of the first seal defines an opening having a stepped shape.

6. The seal assembly according to claim 1, wherein the first seal comprises a cored hole disposed in the proximal end thereof.

7. The seal assembly according to claim 6, wherein the cored hole extends from the third seal and is in communication with the access channel of the first seal.

8. A seal assembly for use with a trocar device, which comprises:
- a housing defining a longitudinal axis and having a passageway therethrough dimensioned to permit passage of a surgical instrument, the housing adapted for mounting to a trocar device;
- a first seal comprising a gel material and being mounted to the housing across the passageway, the first seal including inner seal portions defining an access channel dimensioned to form a substantial sealing relation with and in direct contact with the surgical instrument when advanced along the passageway;
- a second seal comprising a material having a hardness greater than a hardness of the gel material, the second seal fully embedded within the first seal in the absence of the surgical instrument, the second seal including a pair of planar portions tapered inwardly relative to the longitudinal axis; and
- a third seal comprising a fabric material, the third seal disposed at a proximal end of the first seal.

9. The seal assembly according to claim 8 wherein the second seal material comprises an elastomer material.

10. The seal assembly according to claim 8, wherein the second seal is arranged to stabilize the first seal and to receive the surgical instrument in sealed relation with the second seal.

11. The seal assembly according to claim 8, wherein the second seal includes one of a duck-bill seal and a conical seal.

12. The seal assembly according to claim 8, wherein the third seal defines an opening which permits reception of the surgical instrument in sealed relation therewith.

13. The seal assembly according to claim 8, wherein the first seal comprises a cored hole disposed in the proximal end thereof.

14. The seal assembly according to claim 13, wherein the cored hole extends from the third seal and is in communication with the access channel of the first seal.

15. A surgical access device, which comprises:
- an access member defining a central longitudinal axis and having a central opening dimensioned for passage of an object; and
- a seal member mounted to the access member, the seal member defining an access channel to permit passage of the object, the seal member including a first seal, a second seal and a third seal, the first seal comprising a relatively soft gel material defining inner portions dimensioned to form a substantial sealing relation with and in direct contact with the object when advanced along the access channel, the second and third seals being more rigid than the first seal, the second seal embedded within and in direct contact with the first seal in the absence of the object, the second seal arranged to stabilize the seal member and provide a substantial sealed relation with the object, the second seal including one of a duck-bill seal and a conical seal, the third seal disposed at a proximal end of the first seal.

16. The surgical access device according to claim 15 wherein the soft gel material of the first seal comprises one of a urethane gel, a silicone gel, gels incorporating super absorbent polymers, alginates, gum Arabic, polymer hydrogels or a copolymer thereof, or any combination of these materials.

17. The surgical access device according to claim 15 wherein the second seal includes inner portions adapted to permit passage of the object.

18. The surgical access device according to claim 17 wherein the inner portions of the second seal define an opening adapted to form a sealed relation with the object inserted therethrough.

19. The surgical access device according to claim 15 wherein the second seal comprises an elastomer material.

20. The surgical access device according to claim 15 wherein the second seal defines an opening for permitting passage of an object therethrough.

21. The surgical access device according to claim 15 wherein the third seal comprises a fabric material.

22. The surgical access device according to claim 15, wherein the first seal element comprises a cored hole disposed in the proximal end thereof.

23. The surgical access device according to claim 22, wherein the cored hole extends from the third seal and is in communication with the access channel of the seal member.

* * * * *